(12) United States Patent
Waddell et al.

(10) Patent No.: US 10,695,739 B2
(45) Date of Patent: Jun. 30, 2020

(54) CHEMICAL REACTION VESSEL AND SYNTHESIS SYSTEMS AND METHODS

(71) Applicant: PROTEIN TECHNOLOGIES, INC., Tucson, AZ (US)

(72) Inventors: Alexander S. Waddell, Tucson, AZ (US); David W. Ribblett, Tucson, AZ (US); James Cain, Tucson, AZ (US)

( * ) Notice: Subject to any disclaimer, the term of this patent is extended or adjusted under 35 U.S.C. 154(b) by 272 days.

(21) Appl. No.: 15/737,640

(22) PCT Filed: Jun. 16, 2016

(86) PCT No.: PCT/US2016/037911
§ 371 (c)(1),
(2) Date: Dec. 18, 2017

(87) PCT Pub. No.: WO2016/205546
PCT Pub. Date: Dec. 22, 2016

(65) Prior Publication Data
US 2018/0169605 A1     Jun. 21, 2018

Related U.S. Application Data

(60) Provisional application No. 62/182,192, filed on Jun. 19, 2015.

(51) Int. Cl.
| | |
|---|---|
| *B01J 19/08* | (2006.01) |
| *B01J 19/00* | (2006.01) |
| *H05B 6/10* | (2006.01) |
| *C07K 1/04* | (2006.01) |
| *H05B 6/06* | (2006.01) |

(52) U.S. Cl.
CPC ......... *B01J 19/087* (2013.01); *B01J 19/0013* (2013.01); *B01J 19/0046* (2013.01); *B01J 19/0053* (2013.01); *C07K 1/045* (2013.01); *H05B 6/065* (2013.01); *H05B 6/108* (2013.01); *B01J 2219/00211* (2013.01); *B01J 2219/00286* (2013.01); *B01J 2219/00288* (2013.01); *B01J 2219/00484* (2013.01); *B01J 2219/00495* (2013.01); *B01J 2219/00725* (2013.01)

(58) Field of Classification Search
CPC .... B01J 19/087; B01J 19/0013; B01J 19/046; B01J 19/053; C07K 1/045; H05B 6/065; H05B 6/108
USPC ....................................................... 219/618
See application file for complete search history.

(56) References Cited

U.S. PATENT DOCUMENTS

| | | |
|---|---|---|
| 2002/0142454 A1 | 10/2002 | Cracauer et al. |
| 2011/0065150 A1 | 3/2011 | Jones et al. |
| 2011/0116340 A1 | 5/2011 | Gerl et al. |
| 2014/0206841 A1 | 7/2014 | Menakuru et al. |

OTHER PUBLICATIONS

Extended European Search Report issued in relation to European Patent Application EP 16812457.6, dated Sep. 26, 2018 (7 pp).

*Primary Examiner* — Christine J Skubinna
(74) *Attorney, Agent, or Firm* — Quarles & Brady LLP; Yakov Sidorin; Gavin Milczarek-Desai

(57) ABSTRACT

Apparatus and methods utilizing induction-heat energy for heating reactions associated with chemical synthesis, such as peptide synthesis reactions involving activation, deprotection, coupling, and cleavage. Thorough agitation of the contents of reaction vessels during heating, real-time monitoring and adjustment of temperature and/or reaction duration, independent control of different reaction vessels, and scalability are also described.

20 Claims, 10 Drawing Sheets

TOP VIEW

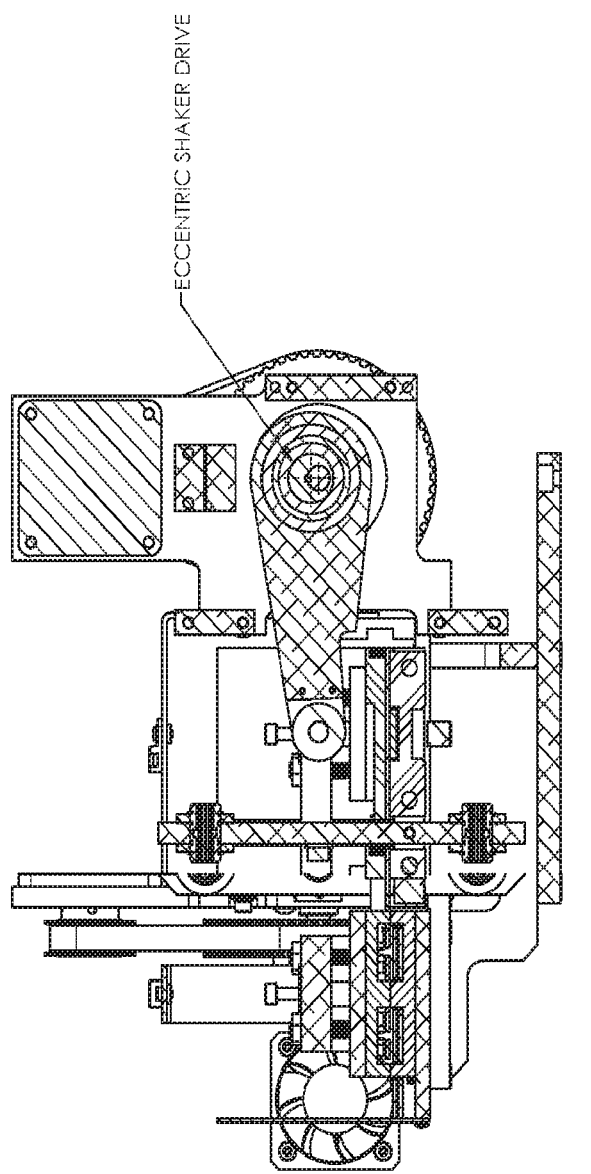

FRONT VIEW

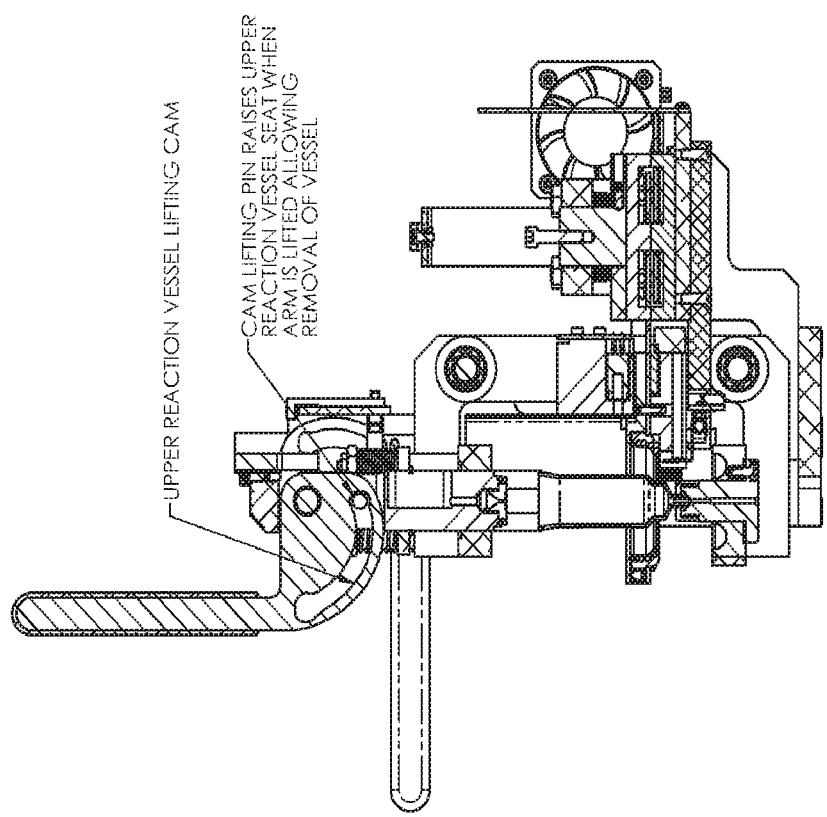

CHEMICAL REACTION VESSEL AND SYNTHESIS SYSTEMS AND METHODS

CROSS-REFERENCE TO RELATED APPLICATIONS

This application represents the U.S. National Stage of International Application No. PCT/US/2016/037911, filed on Jun. 16, 2016, and which claims priority and the benefit of U.S. Provisional Application No. 62/182,192, filed Jun. 19, 2015, the disclosures of which are incorporated by reference herein in their entirety.

BACKGROUND OF THE INVENTION

The application of heat, typically using oil baths, heating elements, or microwaves, has emerged as a tool in the automated chemical synthesis industry. Microwave heating in particular has grown in popularity in recent years, due to the speed with which small volumes can be raised to elevated temperatures.

While microwaves offer rapid heating, there are also a number of considerable disadvantages associated with this technology. All commercial single-mode microwave reactors currently available allow irradiation of only a single vessel. Thus it is not possible to perform microwave synthesis of multiple peptides in parallel. Furthermore, limitations in the reaction vessel and mixing options available on microwave synthesizers make scale-up of microwave conditions practically difficult.

SUMMARY OF THE INVENTION

This disclosure relates to a novel chemical synthesis heating platform and processes involving induction-heat energy. Unlike heating with microwave-based systems, parallel synthesis is possible with an induction heat platform because multiple reaction vessels can be heated with induction simultaneously and the temperature of multiple reaction vessels can be controlled independently. Different types of mixing also are possible, such as nitrogen sparging or oscillation vortex mixing, which ensures that a homogeneous temperature distribution is maintained, making the synthesis operations reliable and scalable.

Various other purposes and advantages will become clear from its description in the specification that follows. Therefore, embodiments described herein include the features hereinafter fully described in the detailed description of the preferred embodiments, and particularly pointed out in the claims. However, such description discloses only some of the embodiments and the various ways in which the described embodiments may be practiced.

BRIEF DESCRIPTION OF THE DRAWINGS

FIG. 5B depicts a cross-sectional view along section C-C of the embodiment shown in FIG. 5A.

FIG. 5D depicts a cross-sectional view along section A-A of the embodiment shown in FIG. 5C.

DETAILED DESCRIPTION

Apparatus and methods utilizing induction-heat energy for heating reactions associated with chemical synthesis, such as, for example, peptide synthesis reactions involving activation, deprotection, coupling, and cleavage. Thorough agitation of the contents of reaction vessels during heating and real-time monitoring and adjustment of temperature and/or reaction duration are also described.

Figure 1:
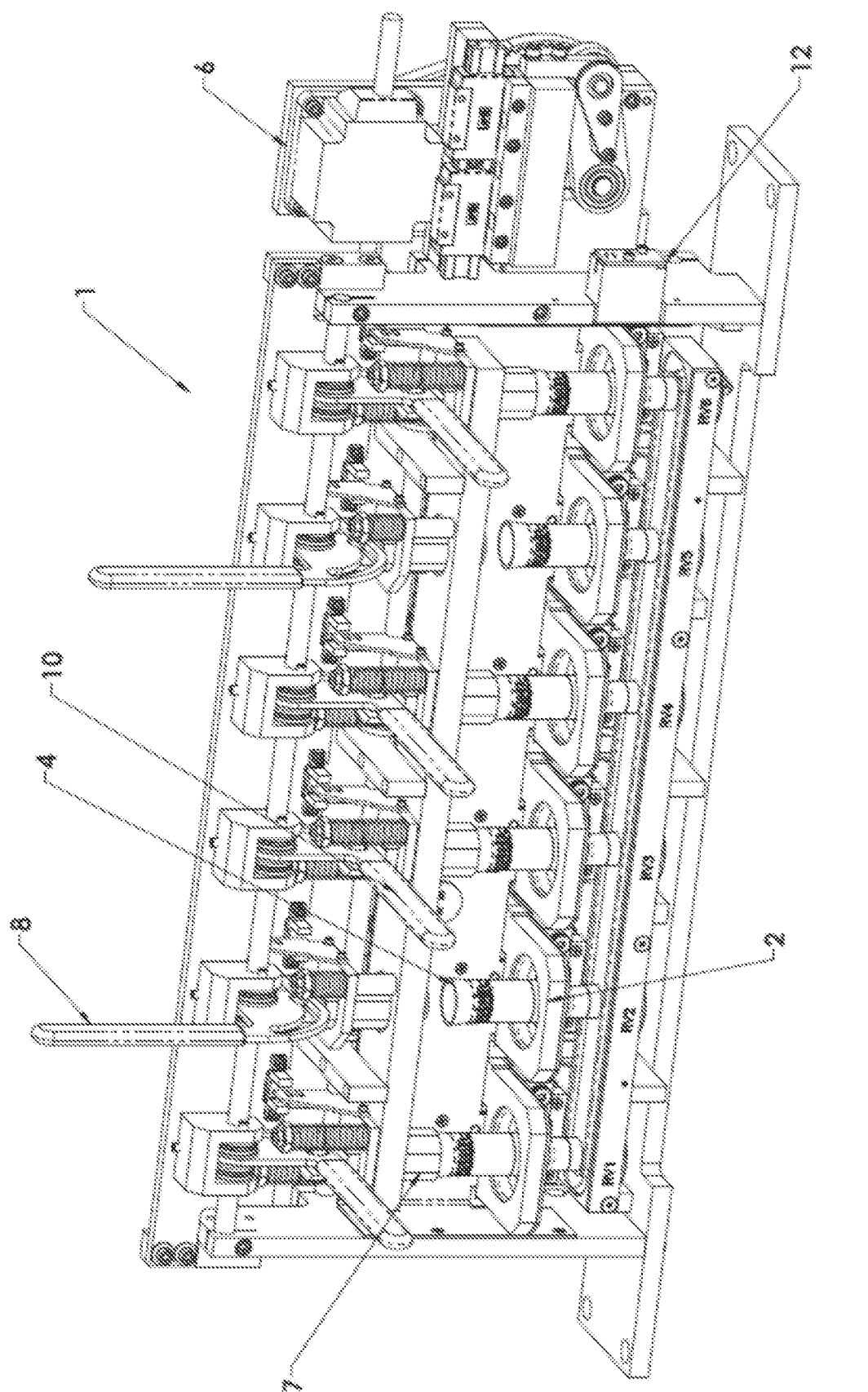
FIG. 1 is a front perspective of an embodiment.
Figure 2:
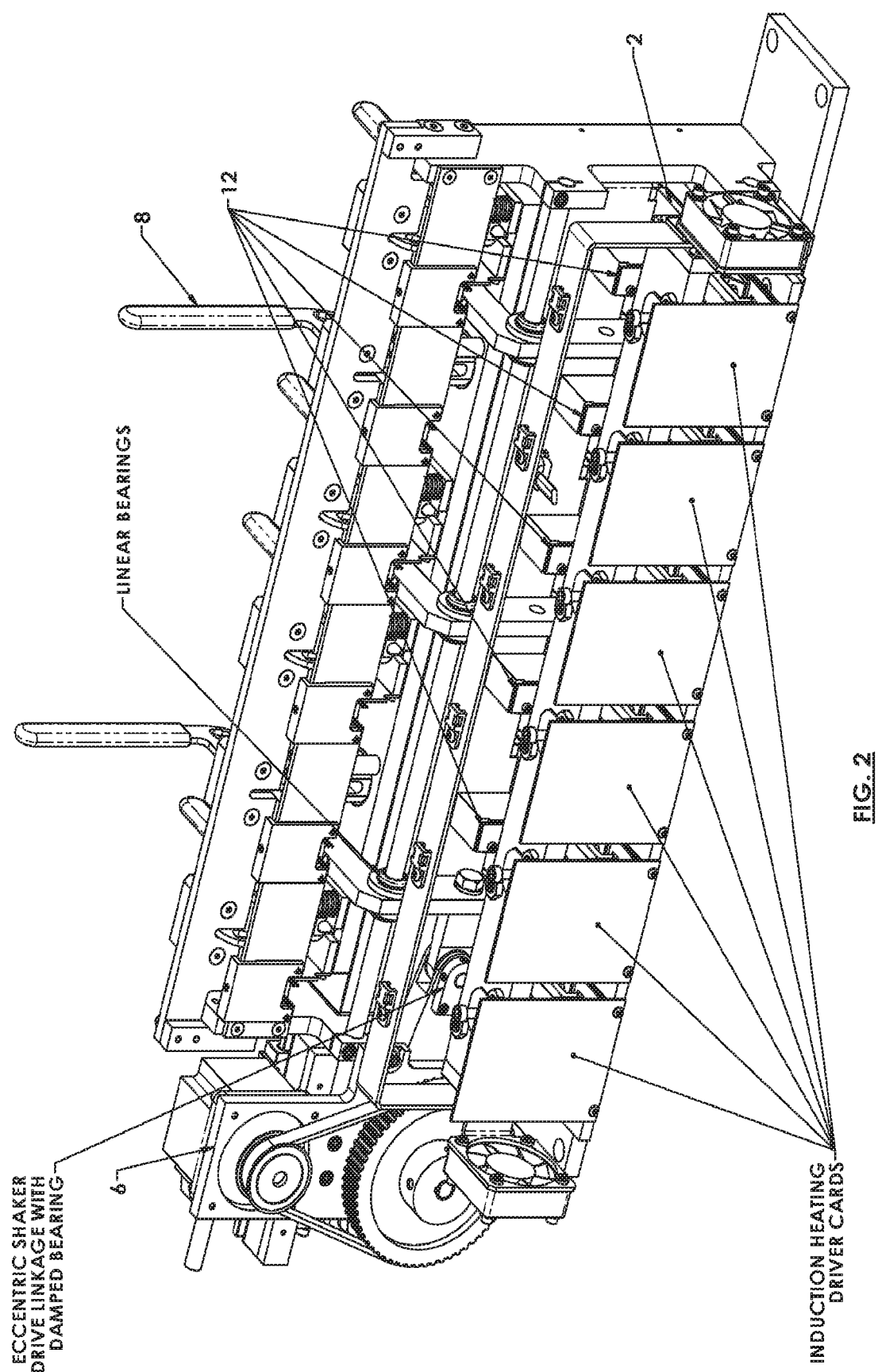
FIG. 2 is a back perspective view of the embodiment in FIG. 1.

Turning to FIGS. 1 and 2, a chemical synthesis reaction-heating platform 1 is depicted. The platform includes a source of induction-heat energy 2 (such as a free floating induction coil) configured to heat a content of one or more reaction vessels 4. Furthermore, the platform 1 is configured to shake or mix the one or more reaction vessels 4 during heating through, for example, a mixer drive assembly 6 including an eccentric shaker drive linkage with a damped bearing that moves each vessel through connection to an adjustable interface 7 (shown in an "open" or disconnected state 8 or in a "closed" or connected state 10).

Preferably, the motion conveyed by the mixer drive assembly 6 is an oscillating harmonic motion which creates a vortex motion in the liquid in the reaction vessel. However, different mixing methods and motions are possible, as are configurations and attachment point of the interface and/or the shaking or mixing mechanism for each vessel. Also, according to this embodiment, the vessels 4 are coupled with the interfaces 7 such that during heating one or more reaction vessels are free from contact with said source of induction-heat energy. Thus, in the depicted free-floating induction coil platform, the associated reaction vessel is moved synchronously to thereby maintain a desired field alignment and distance parameter(s).

In order to better control the heating of a vessel 4, a pyrometer 12 may be disposed in proximity. Preferably, the pyrometer is an infrared (IR) sensor that connects to a controller and thereby provides for temperature adjustment. While only one pyrometer is shown in FIG. 1 for simplicity, each vessel 4 can be paired with a temperature sensor as shown in FIG. 2 such that the temperature of each vessel can be independently controlled.

Figures 3A, 3B:
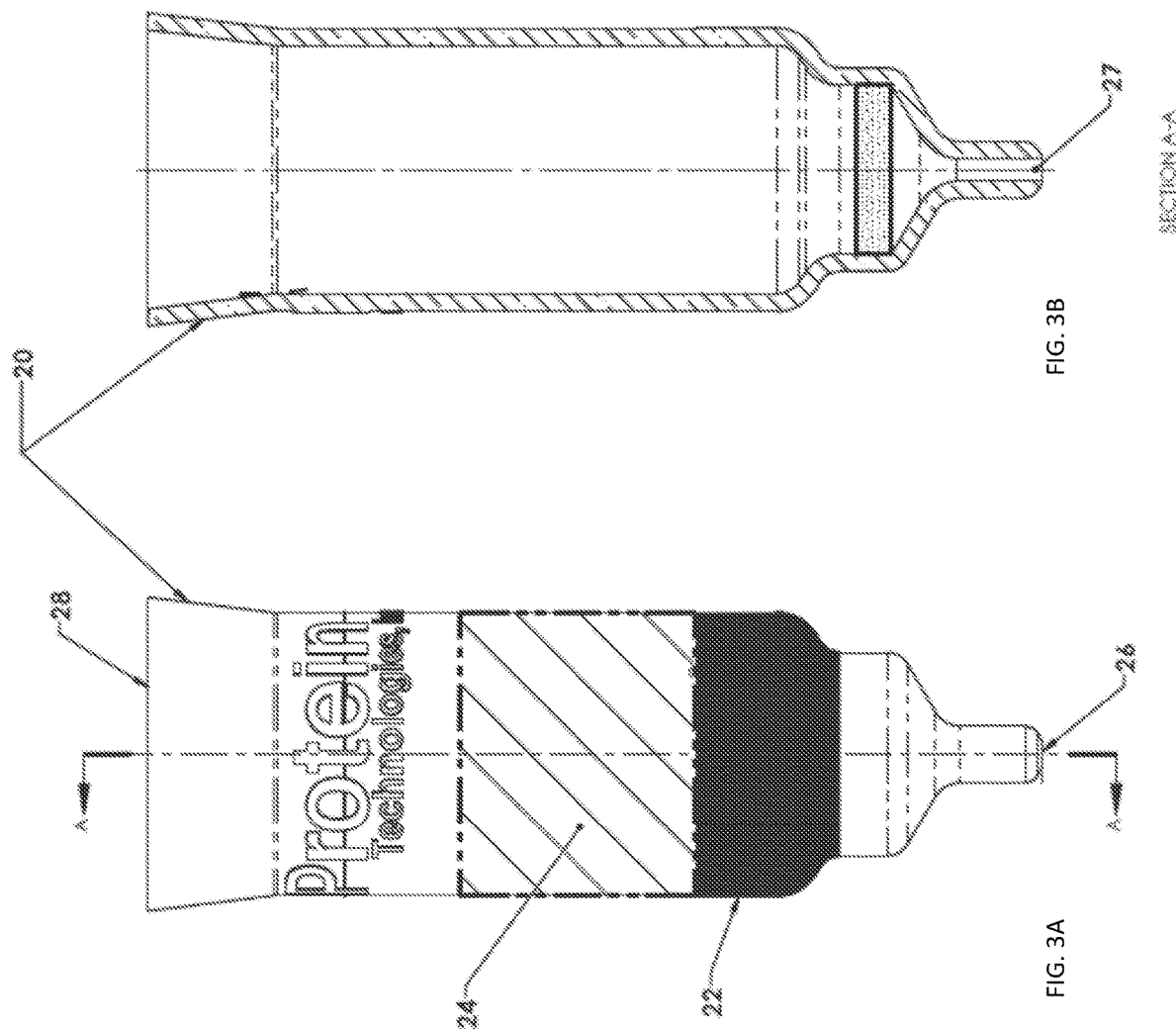
FIG. 3A is a close-up view of a single reaction vessel assembly showing in better detail the conductive coating and surface configuration that diffuses IR radiation.
FIG. 3B is a cross-sectional view of FIG. 3A along line A-A.

Turning to FIGS. 3A and 3B, a reaction vessel 20 is depicted in front elevational view and in cross section along the axis defined by A-A. In order to be heated through induction, the reaction vessel 20 is coated with a heat-conductive material 22. While such material preferably is a metal (of which several could be used), DUPONT 7713 conductor paste baked onto glass vessels has shown to be especially effective in producing heat. The heat-conductive material may include a plurality of layers, with the inventors finding between 3-5 layers to be more effective.

In conjunction with the pyrometer (e.g., infrared heat temperature sensor), the reaction vessels preferably are configured to diffuse and homogenize IR radiation. Such configuration may, for example, be accomplished by chemical etching, physical abrasion, or various glass bead grit 24 to diffuse and homogenize the IR radiation. Each vessel 20, in this embodiment, has a bottom 26 featuring, in this case, an elongated opening 27 for fluid transfer and a top 28 that can be coupled with an interface 7.

Thus, in this embodiment, the reaction vessel 20 is held in place between the interface 7 and a lower vessel seat under spring force (see detail in FIGS. 5A-5E). The interface 7 and the lower vessel seat may contain a channel, valving, etc., for accomplishing fluid transfer through opening 27 and/or through the top of vessel 20 (see detail in FIGS. 5A-5E).

Figure 4:
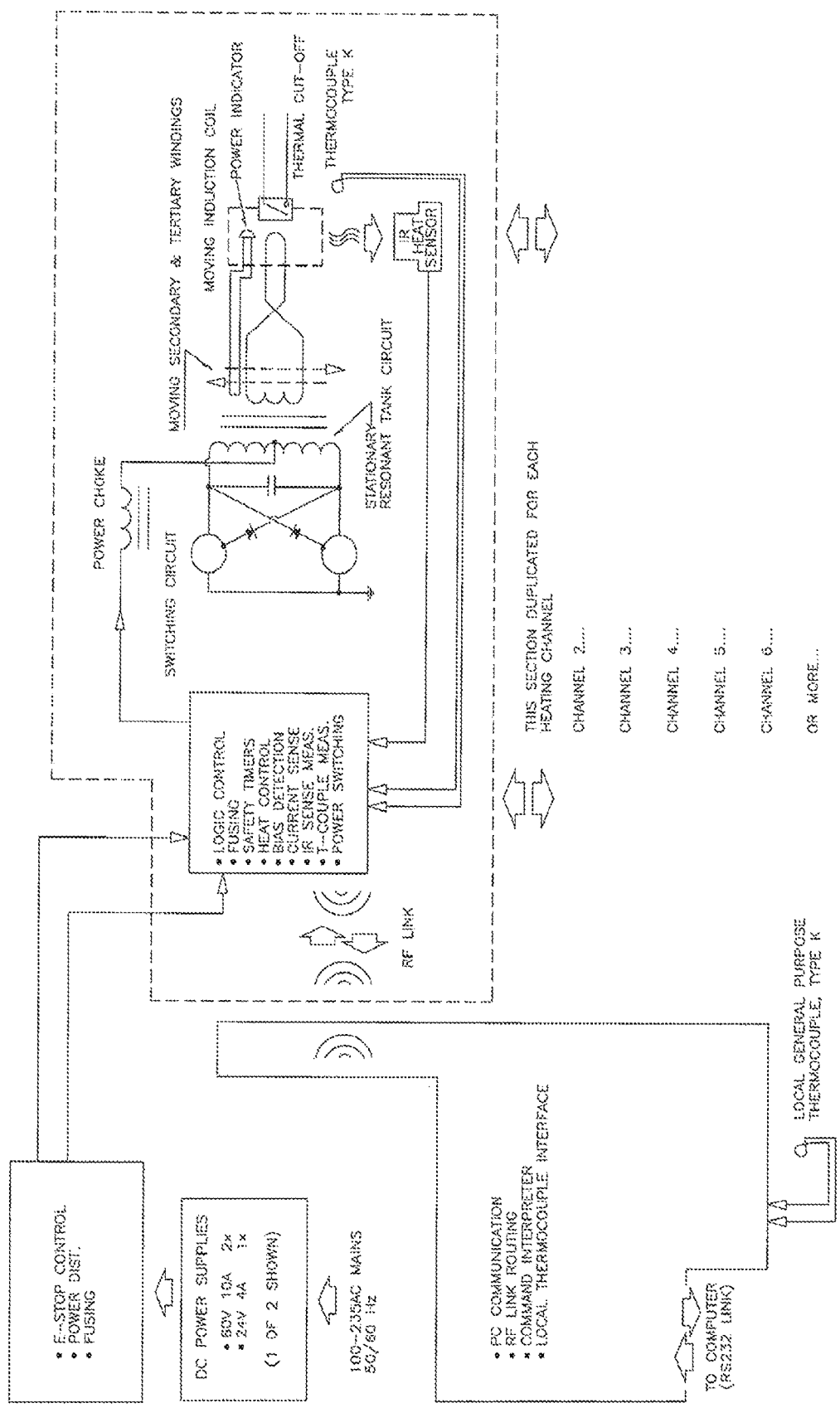
FIG. 4 depicts a basic electrical and control schematic for an embodiment.
Figure 5A:
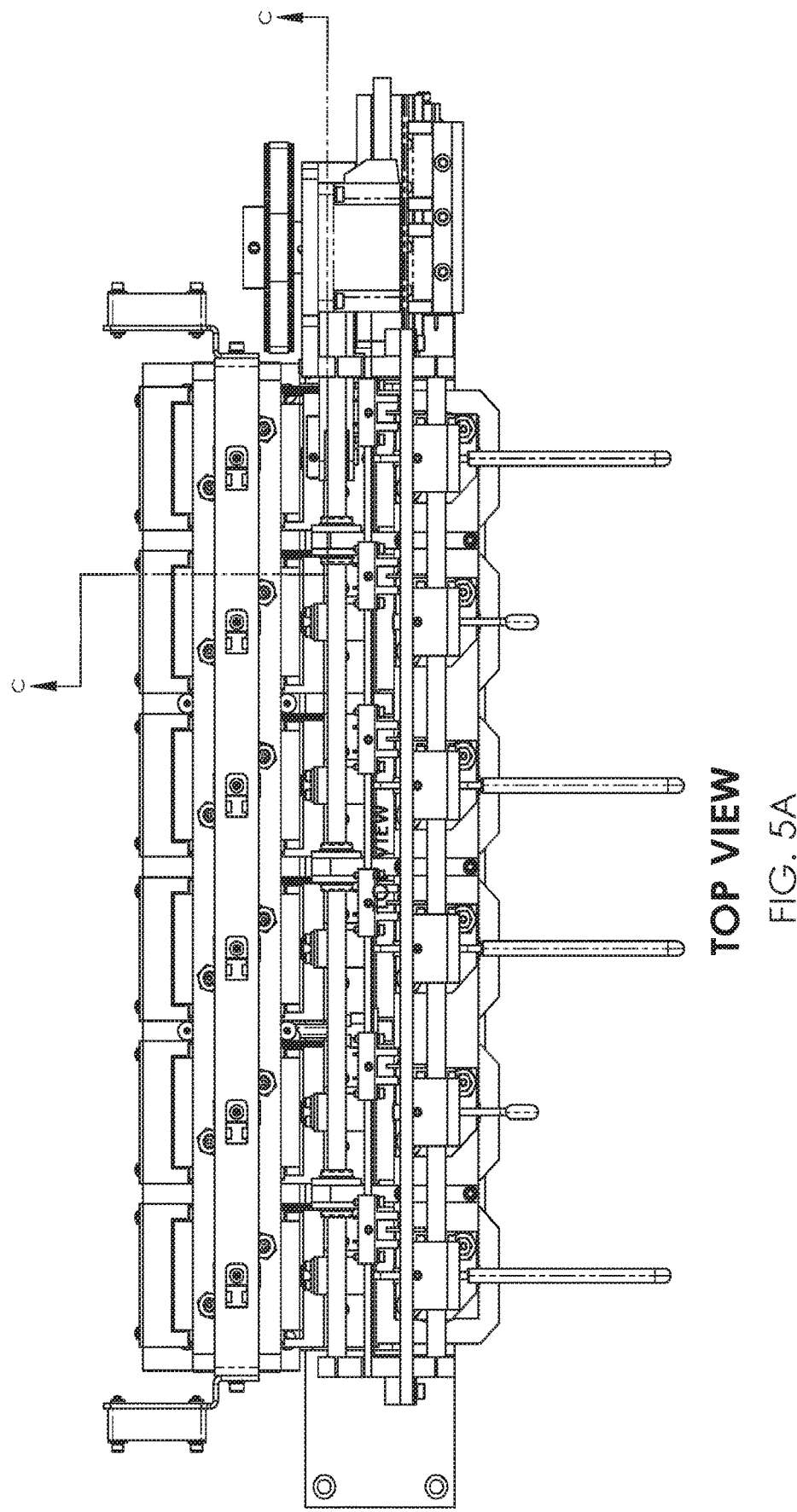
FIG. 5A depicts a top view and further details of the embodiment shown in FIG. 1
Figure 5C:
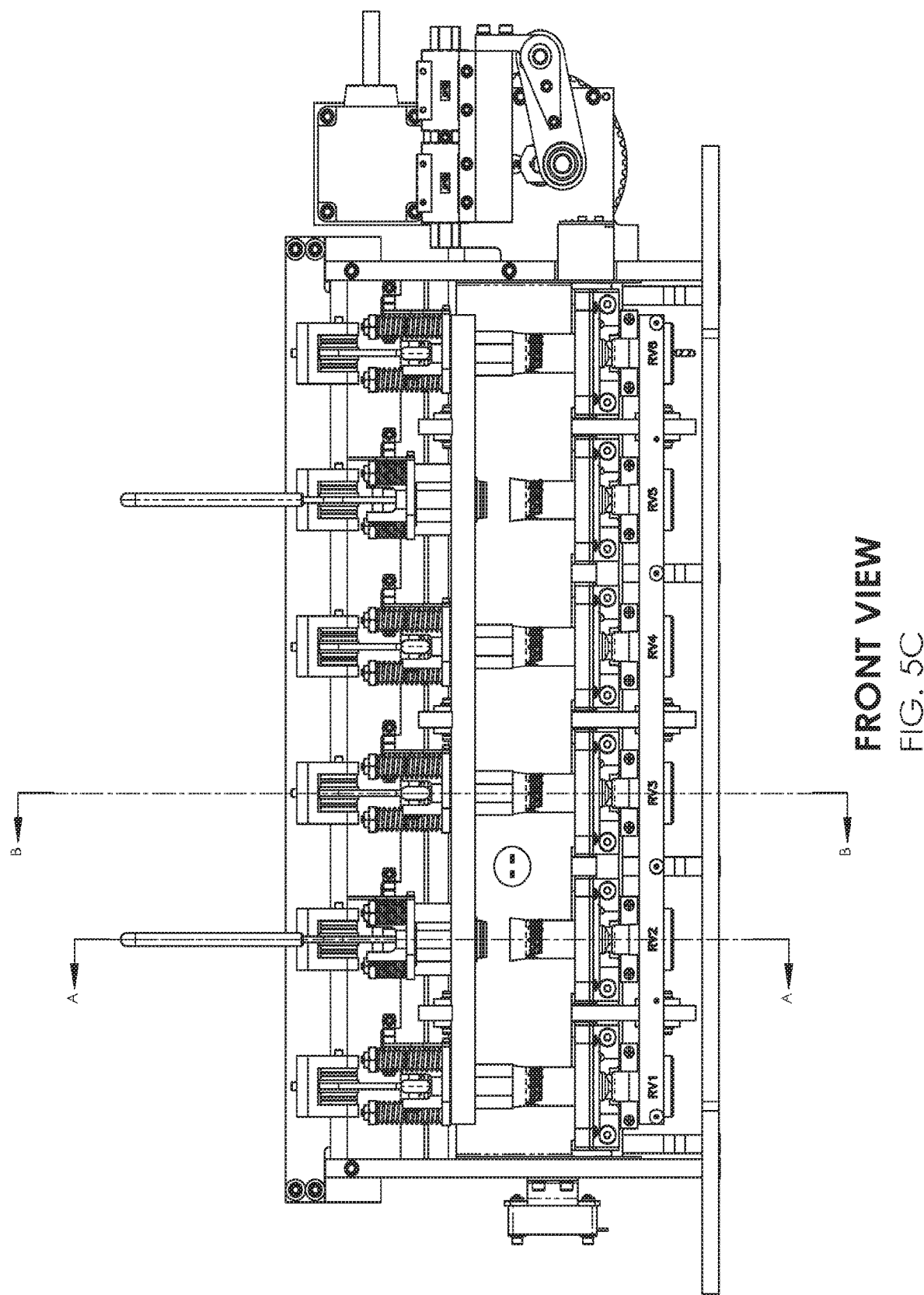
FIG. 5C depicts a front view and further details of the embodiment shown in FIG. 1
Figure 5E:
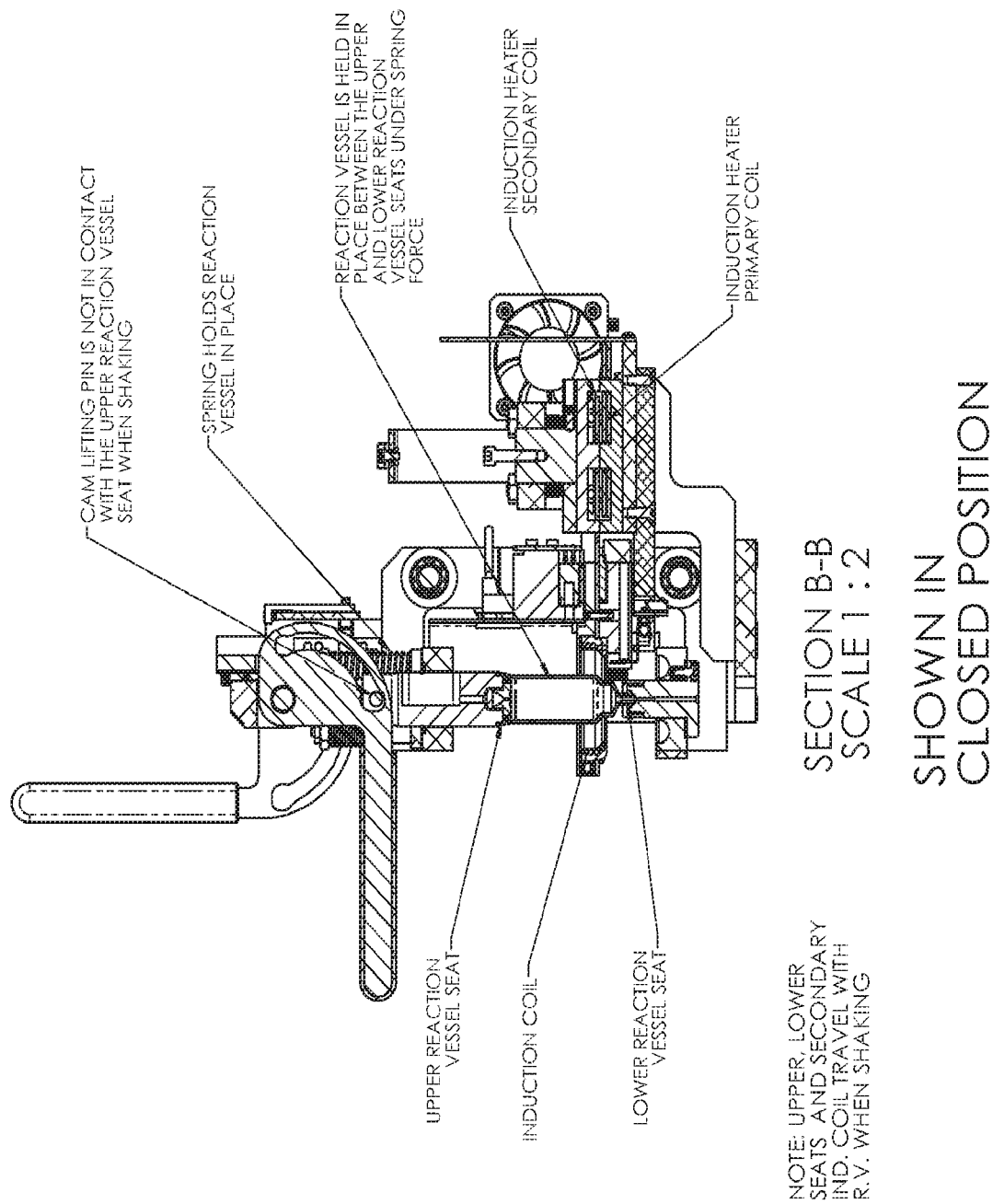
FIG. 5E depicts a cross-sectional view along section B-B of the embodiment shown in FIG. 5C.

As shown schematically in FIG. 4, the platform 1 preferably further includes a controller configured to control temperature of more than one reaction vessel independently. Moreover, independent controllers and power amplifiers configured to control the temperature of one or more selected reaction vessels (see the "section duplication" portion of FIG. 4 schematic, which provides for multiple controllers and power amplifiers) can be utilized through, for example, programming contained on a non-transient readable storage medium of a computer. Of course, other automated features and functions may be programmed as well.

Figure 6:
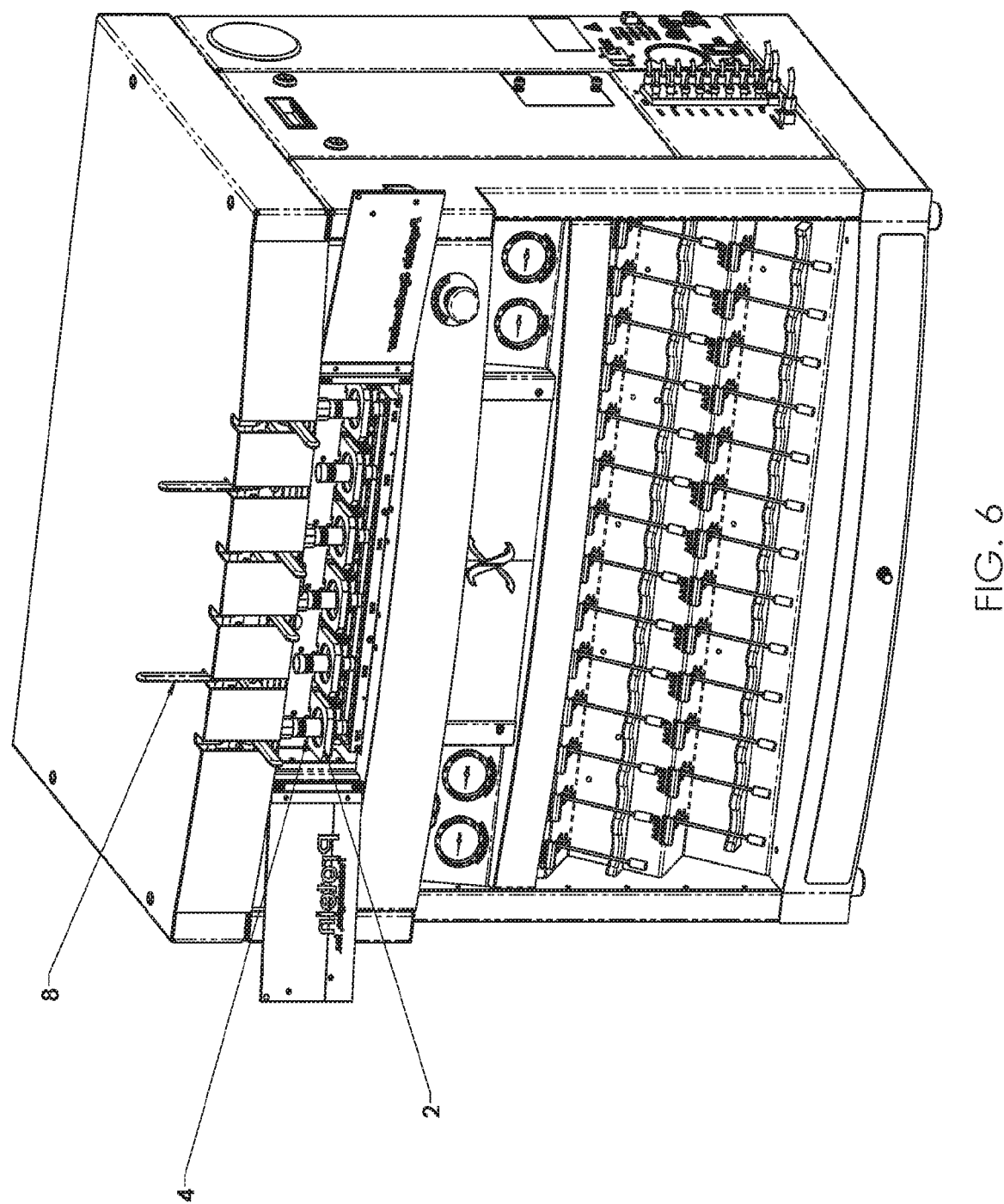
FIG. 6 is a front perspective view of a complete instrument such as could be used for peptide synthesis and modified to include the inventive heating platform.

Indeed, the platform embodiment described above can be used in specialized instruments, such as those designed for solid phase peptide synthesis (SPPS) (FIG. 6). For examples of the components and configuration of such instruments, see U.S. Pat. No. 5,203,368 or a Prelude® automated peptide synthesizer sold by Protein Technologies, Inc., Tucson, Ariz.

In one embodiment (FIG. 6), the instrument for solid phase peptide synthesis includes an induction-heat energy platform 1 for one or more reaction vessels 4 and a source of induction-heat energy 2 configured to heat a content of the one or more reaction vessels, with the one or more reaction vessels being coated with a heat-conductive material, the platform is configured to shake or mix through motion the one or more reaction vessels during heating, and one or more of valving, channels, hoses, etc., that are operably configured for actuating and controlling fluid transfers as necessary for peptide synthesis.

The term "peptide" or "peptides" includes synthetic versions of naturally occurring peptides, and peptoids, peptide-nucleic acids, and peptide mimics that include non-natural, (e.g. enantiomeric) amino acids, amino acid derivatives (e.g., molecules with modified side chains), beta-amino acids, and other similar such molecules.

Processes for chemical synthesis using induction-heat energy also are provided. In one embodiment, the method includes applying induction-heat energy to a reaction vessel during a synthesis operation while shaking or mixing (for example, through motion) the reaction vessel, with the heating preferably being performed in a manner such that the reaction vessel is free from contact with the source of induction-heat energy. The method can further include monitoring temperature in the reaction vessel in real time and adjusting an output of the induction-heat energy to a predetermined point.

In a method embodiment for the solid phase synthesis of peptides, the following steps are performed: deprotection while agitating and heating a reaction vessel containing an amino acid and deprotection reagents with a source of induction-heat energy, activating and coupling a second amino acid to a deprotected amine of said amino acid while agitating and heating said reaction vessel with a source of induction-heat energy, and performing successive deprotection and coupling steps as above until a desired peptide is synthesized.

Non-Limiting Examples

Testing with a volume of water shows heating is as fast or faster than microwave heating for a 40 ml reaction vessel.

Single peptide synthesis with induction-heat energy for the Jung-Redemann "JR 10-mer" WFTTLISTIM.

Synthesis: The JR 10-mer peptide was synthesized on the Prelude X™ peptide synthesizer at 50 µmol scale using Rink amide MBHA resin (loading 0.32 mmol/g). Deprotection was performed with 20% piperidine in DMF for 1 minute at 90° C. After deprotection the resin was washed with DMF for 4×30 seconds. Coupling was performed using 0.25 mmol AA (5 eq), 0.25 mmol HCTU (5 eq), and 0.5 mmol NMM (10 eq) in DMF for 2 minutes at 90° C. No washes were used after coupling. For cleavage, the resin was treated with 95/2.5/2.5 TFA/TIS/H$_2$O for two hours at room temperature. After precipitation in ice-cold ether, the crude peptide was dried overnight.

Analysis: The resulting crude peptide was dissolved in 50/50 water/acetonitrile solution and analyzed on a Shimadzu Prominence HPLC using a C18, 300 Å, 5 um, 250×4.6 mm column (Microsorb-MV), over 60 minutes with a flow rate of 1.5 mL/min, and using a gradient of 5-95% B, where Buffer A is 0.1% TFA in water, and Buffer B is 0.1% TFA in acetonitrile. Detection was at 214 nm. Mass analysis was performed on a Shimadzu LCMS-2020 Single-Quad mass spectrometer, equipped with a C18, 100 Å, 2.6 um, 50×2.1 mm column (Phenomenex Kinetex), over 7 minutes with a flow rate of 1 mL/min and using a gradient of 5-50% B where Buffer A is 0.1% formic acid in water and Buffer B is 0.1% formic acid in acetonitrile.

Results: The peptide commonly referred to as JR 10-mer was synthesized using rapid induction heating during the deprotection and coupling reactions on the Prelude X™ peptide synthesizer. LC-MS and HPLC analysis indicated that the correct peptide was obtained with a crude purity of 66%. This is a substantial improvement over the results found with a room temperature synthesis, which with an otherwise equivalent protocol produced a peptide with a crude purity of only 15%. These results are clear evidence of the benefits of applying rapid induction heating during the synthesis of difficult peptide sequences like the JR 10-mer.

Parallel peptide synthesis with induction-heat energy of the Jung-Redemann "JR 10-mer" WFTTLISTIM.

Synthesis: The JR 10-mer peptide was synthesized in six vessels in parallel on the Prelude X™ peptide synthesizer at 50 µmol scale using three protocols (room temperature, 60° C. for deprotection and coupling, 90° C. for deprotection and coupling) in duplicate. The solid support used was Rink amide MBHA resin (loading 0.32 mmol/g). Deprotection was performed with 20% piperidine in DMF for 1 minute at room temperature, 60° C., or 90° C. After deprotection the resin was washed with DMF for 4×30 seconds. Coupling was performed using 0.25 mmol AA (5 eq), 0.25 mmol HCTU (5 eq), and 0.5 mmol NMM (10 eq) in DMF for 2 minutes at room temperature, 60° C., or 90° C. No washes were used after coupling. For cleavage, the resin was treated with 95/2.5/2.5 TFA/TIS/H$_2$O for two hours at room temperature. After precipitation in ice-cold ether, the crude peptide was dried overnight.

Analysis: The resulting crude peptides were dissolved in 50/50 water/acetonitrile solution and analyzed on a Shimadzu Prominence HPLC using a C18, 300 Å, 5 um, 250×4.6 mm column (Microsorb-MV), over 60 minutes with a flow rate of 1.5 mL/min, and using a gradient of 5-95% B, where Buffer A is 0.1% TFA in water, and Buffer B is 0.1% TFA in acetonitrile. Detection was at 214 nm. Mass analysis was performed on a Shimadzu LCMS-2020 Single-Quad mass spectrometer, equipped with a C18 100 Å, 2.6 um, 50×2.1 mm column (Phenomenex Kinetex), over 7 minutes with a flow rate of 1 mL/min and using a gradient of 5-50% B where Buffer A is 0.1% formic acid in water and Buffer B is 0.1% formic acid in acetonitrile.

Results: The peptide commonly referred to as JR 10-mer was synthesized at room temperature and using rapid induction heating during the deprotection and coupling reactions on the Prelude X™ peptide synthesizer at the indicated temperatures. LC-MS analysis indicated that the correct peptide was obtained in all cases, however the crude purity varied substantially. At room temperature, purities of just 15% were obtained in both duplicate runs. Heating to 60° C. during the deprotection and coupling reactions improved the purities to 48% and 46% in the two vessels. The best results were observed by raising the temperature to 90° C. for the deprotections and couplings, providing crude purities of 66% and 61% for the duplicate syntheses. These results are clear evidence of the benefits of applying rapid induction heating during the synthesis of difficult peptide sequences like the JR 10-mer.

Typical embodiments of the invention have been disclosed in the drawings and specifications. The use of specific terms is employed in a descriptive sense only, and these terms are not meant to limit the scope of the invention being set forth in the following claims. All publications cited herein are hereby incorporated by reference.

What is claimed is:

1. A chemical synthesis reaction-heating platform, comprising:
   one or more reaction vessels, and
   a source of induction-heat energy configured to heat a content of said one or more reaction vessels,
   wherein said one or more reaction vessels is coated with a heat-conductive material that comprises a plurality of layers of a metal conductor paste, and
   wherein said platform is configured to shake or mix said content in the one or more reaction vessels during a process of heating said content.

2. The platform of claim 1, wherein said platform is configured to shake or mix through motion said one or more reaction vessels during heating in a manner such that said one or more reaction vessels are free from contact with said source of induction-heat energy.

3. The platform of claim 1, wherein said heat-conductive material comprises three to five layers of DUPONT 7713 conductor paste baked onto said one or more reaction vessels.

4. The platform of claim 1, wherein said platform further includes an infrared (IR) heat temperature sensor and said one or more reaction vessels is configured to diffuse and homogenize IR radiation.

5. The platform of claim 4, wherein said one or more reaction vessels contains a surface dimensioned to diffuse and homogenized IR radiation.

6. The platform of claim 1, further including a controller configured to control temperatures of more than one reaction vessels independently.

7. The platform of claim 1, further including independent controllers and power amplifiers configured to control temperatures of one or more selected reaction vessels.

8. The platform of claim 1, wherein induction source of induction-heat energy comprises a free-floating induction coil, said induction coil and associated reaction vessel being configured such that each moves synchronously to thereby maintain desired field alignment and distance parameter.

9. An instrument for solid phase peptide synthesis, comprising:
   one or more reaction vessels, and
   a source of induction-heat energy configured to heat a content of said one or more reaction vessels, and
   means for actuating and controlling fluid transfers and heating necessary for peptide synthesis;
   wherein said one or more reaction vessels is coated with a heat-conductive material that contains a plurality of layer of a metal conductor paste, and
   wherein said instrument is configured to shake or mix said content of the one or more reaction vessels during a process of heating of said content.

10. The instrument of claim 9, wherein said platform is configured to shake or mix through motion said one or more reaction vessels during said process of heating in a manner such that said one or more reaction vessels are free from contact with said source of induction-heat energy.

11. The instrument of claim 9, wherein said heat-conductive material comprises three to five layers of DUPONT 7713 conductor paste baked onto said one or more reaction vessels.

12. The instrument of claim 9, wherein said platform further includes an infrared (IR) heat temperature sensor and said one or more reaction vessels is configured to diffuse and homogenize IR radiation.

13. The instrument of claim 12, wherein said one or more reaction vessels contains a surface dimensioned to diffuse and homogenized IR radiation.

14. The instrument of claim 9, further including a controller configured to control temperatures of more than one reaction vessels independently.

15. The instrument of claim 9, further including independent controllers and power amplifiers configured to control temperatures of one or more selected reaction vessels.

16. The instrument of claim 9, wherein said source of induction-heat energy comprises a free-floating induction coil, said induction coil and associated reaction vessel being configured such that each moves synchronously to thereby maintain desired field alignment and distance parameter.

17. The instrument of claim 13, wherein said one or more reaction vessels includes a bottom with an opening that is dimensioned to transfer a fluid from said one or more reaction vessels.

18. An instrument for solid phase peptide synthesis, comprising:
   one or more reaction vessels, and
   a source of induction-heat energy configured to heat contents of said one or more reaction vessels,
   wherein said one or more reaction vessels is coated with a heat-conductive material,
   means for actuating and controlling fluid transfers and heating necessary for peptide synthesis,
   and
   an infrared (IR) heat temperature sensor,
   wherein said one or more reaction vessels is configured to diffuse and homogenize IR radiation,
   and
   wherein said instrument is configured to shake or mix said contents of the one or more reaction vessels during a process of heating of said contents.

19. The instrument of claim 18, wherein said heat-conductive material comprises a plurality of layers of metal conductor paste.

20. The instrument of claim 18, including a controller configured to control temperatures of more than one from said one or more reaction vessels independently.

\* \* \* \* \*